(12) United States Patent
Knapp (10) Patent No.: US 7,654,989 B2
(45) Date of Patent: Feb. 2, 2010

(54) URETERAL ACCESS SHEATH

(75) Inventor: Tracey E. Knapp, Lawrenceville, GA (US)

(73) Assignee: C. R. Bard, Inc., Murray Hill, NJ (US)

(*) Notice: Subject to any disclaimer, the term of this patent is extended or adjusted under 35 U.S.C. 154(b) by 1266 days.

(21) Appl. No.: 10/409,527

(22) Filed: Apr. 8, 2003

(65) Prior Publication Data
US 2004/0204629 A1 Oct. 14, 2004

(51) Int. Cl.
*A61M 25/00* (2006.01)
(52) U.S. Cl. ................................... 604/284
(58) Field of Classification Search .......... 604/264, 604/523–539, 284
See application file for complete search history.

(56) References Cited

U.S. PATENT DOCUMENTS

| 4,557,255 | A |   | 12/1985 | Goodman |
| 4,741,326 | A |   | 5/1988  | Sidall et al. ............ 128/4 |
| 4,798,193 | A |   | 1/1989  | Giesy et al. |
| 4,802,461 | A |   | 2/1989  | Cho |
| 4,834,702 | A |   | 5/1989  | Rocco |
| 4,899,733 | A |   | 2/1990  | DeCastro et al. |
| 5,127,393 | A |   | 7/1992  | McFarlin et al. |
| 5,199,417 | A |   | 4/1993  | Muller et al. |
| 5,324,306 | A | * | 6/1994  | Makower et al. .......... 606/213 |
| 5,391,155 | A |   | 2/1995  | Sachse |
| 5,483,951 | A |   | 1/1996  | Frassica et al. |
| 5,569,215 | A |   | 10/1996 | Crocker |
| 6,395,021 | B1 |  | 5/2002  | Hart et al. |
| 6,440,123 | B1 |  | 8/2002  | Engel .................. 606/2.5 |
| 7,150,737 | B2 | * | 12/2006 | Purdy et al. ............ 604/506 |
| 2001/0027295 | A1 | | 10/2001 | Dulak et al. |
| 2002/0038115 | A1 | | 3/2002  | Dulak et al. |
| 2002/0188175 | A1 | | 12/2002 | Levine et al. |
| 2003/0114732 | A1 | | 6/2003  | Webler et al. |

FOREIGN PATENT DOCUMENTS

EP 0515119 A1 11/1992

* cited by examiner

*Primary Examiner*—Manuel A Mendez
(74) *Attorney, Agent, or Firm*—Rutan & Tucker, LLP (57) ABSTRACT

A ureteral access sheath comprises a sheath assembly having a main lumen and one or more secondary lumens. The sheath assembly can be configured with medical devices in both lumens, for example, a ureteroscope in the main working channel, and a guidewire, stone basket, grasper, laser fiber, or other surgical instrument in the secondary working channel. Or the sheath assembly can be configured with a medical device in one channel and the other lumen coupled to an irrigation means, such that irrigation of the surgical field can be efficiently accomplished even though the main working channel is substantially completely occupied by, e.g., a ureteroscope. Or the sheath assembly can be configured for irrigation through one lumen and aspiration through the other lumen, thereby creating a turbulent flow which washes the surgical field to facilitate removal of particles and debris.

18 Claims, 14 Drawing Sheets

URETERAL ACCESS SHEATH

TECHNICAL FIELD

The present invention relates generally to surgical devices and relates more specifically to a ureteral access sheath for creating an access channel from the external meatus to a location within the ureter of a patient.

BACKGROUND OF THE INVENTION

It is known to use a ureteral access sheath for creating an access channel from the external meatus to a location within the ureter of a patient to perform surgical procedures within the ureter and/or kidney. With an established channel to the ureter, a surgeon is able to insert and to withdraw a ureteroscope or other instrument more rapidly and with limited trauma to a patient's urinary system.

A typical prior art ureteral access sheath includes two subassemblies: a dilator and a sheath. The dilator is placed within the sheath, and the dilator and sheath combination is advanced through the urethra, through the bladder, and to the ureter. The dilator is then withdrawn, leaving the sheath in place. A ureteroscope is then advanced through the sheath to access the ureter.

A problem with known prior art ureteroscopic procedures concerns the need to irrigate the target site. Irrigation is critical during most ureteroscopic procedures. Since the inability to view the surgical area could have devastating effects, a procedure will not be continued until adequate viewing is achieved. Typically, irrigation fluid is supplied through the working channel of the ureteroscope. Because other instruments (i.e., a stone basket, grasper, laser fiber, etc.) also occupy the working channel, the flow rate of the irrigation fluid is reduced in proportion to be diameter of the instrument being used. Thus it would be desirable to provide a surgical environment in which the flow rate of irrigation fluid is not restricted by the presence of instruments within the working channel of the ureteroscope.

An additional problem with known prior art ureteral access sheaths concerns the need for guidewires in conjunction with the placement of the sheath. To use a typical prior art ureteral access sheath, the physician performs the following steps:

1. A cystoscope is inserted into the patient's urethra and advanced into the bladder, where the ureteral orifices are identified.
2. Using the cystoscope, a guidewire is inserted into the ureteral orifice.
3. Using fluoroscopy, the proximal end of the guidewire is inserted through the ureter and into the kidney.
4. With the guidewire carefully held in place, the cystoscope is removed over the guidewire.
5. The dilator is placed within the sheath.
6. The distal end of the ureteral access sheath is now back-loaded onto the proximal end of the guidewire and advanced over the guidewire and into the ureter. Advancement and position of the ureteral access sheath is usually verified with fluoroscopy.
7. The dilator is removed from the sheath.

Now the sheath is in place to provide a working channel from outside the patient to the ureter. However, on occasion a surgical procedure may inadvertently puncture or lacerate the ureter. Normally, a secondary "safety wire" has been placed for access, in the event the access sheath needs to be adjusted or otherwise removed.

The safety wire is normally placed alongside the sheath. Placement of the secondary safety wire requires a number of additional steps:

8. The safety wire is inserted into the lumen of the sheath and advanced into the kidney.
9. With both the original guidewire and the safety wire held in place, the sheath is removed.
10. The dilator is placed into the sheath.
11. The sheath is back-loaded onto the initial guidewire as explained before and advanced into the ureter.
12. The dilator is removed from the sheath.

At this juncture, the sheath is in place, the original guidewire is disposed within the sheath, and the safety wire runs along the outside of the sheath. However, because the original guidewire occupies the same channel of the sheath into which the ureteroscope will be inserted, the original guidewire must now be removed before a surgical procedure can be commenced. Hence, 13. The guidewire is removed from the sheath.

As can be seen, the requirement for a safety wire located outside the working channel of the sheath adds a number of steps and additional time and complexity to the procedure of positioning the sheath. In addition, the presence of the safety wire within the ureter alongside the sheath increases the possibility of lacerating the ureter.

In addition, some surgical procedures require the removal from the ureter of objects that are larger than the lumen of the sheath. In such instances, the objects are grasped against the distal end of the sheath, and the sheath must be completely withdrawn from the patient to extract the object. The sheath may be repositioned by once again placing the dilator into the sheath and advancing the sheath over the safety wire. However, there is now no safety wire running alongside the sheath. To position another safety wire alongside the sheath, the sequence of steps previously set forth must be repeated.

Thus there is a need for a ureteral access sheath which minimizes the number of steps required to position the sheath.

There is a further need for an improved ureteral access sheath which facilitates the placement of a safety wire.

SUMMARY OF THE INVENTION

Stated generally, the present invention comprises a ureteral access sheath which addresses the described shortcomings of prior art ureteral access sheaths such as those described above. Like the prior art devices, the proposed ureteral access sheath comprises two separate components: a sheath and a dilator. However, the proposed sheath differs from known prior art devices in that it comprises multiple lumens—a main working channel and one or more secondary lumens. A secondary lumen integral with the ureteral access sheath can be used to irrigate the surgical field. Thus it is not necessary to rely upon the working channel of the ureteroscope, typically occupied by a surgical device, for irrigation. Additionally, the secondary lumen can be used to accommodate a safety wire. The guidewire is received within the main working channel of the ureteral access sheath. The safety wire can be introduced through the secondary lumen, while the main guidewire is removed from the working channel to, for instance, accommodate the ureteroscope. The safety wire can simply remain in place via the secondary lumen. Alternatively the safety wire can remain outside the sheath in a manner analogous to existing practices.

According to one embodiment, the sheath comprises two lumens: the working channel and a secondary lumen for accommodating the safety wire or providing an irrigation channel (or both). According to a second embodiment, the sheath comprises at least three lumens: the working channel, a first secondary lumen for use as an irrigation channel, and a second secondary lumen for accommodating the safety wire.

To use the proposed ureteral access sheath, the guidewire is positioned, and the dilator is loaded into the sheath as set forth in steps 1-5 above. The guidewire is likewise threaded through the working channel of the sheath. Once the sheath has been advanced over the guidewire and into position, the safety wire may be threaded through the secondary lumen. The main guidewire can be removed for use of instruments through the working channel, with the safety wire providing the ability to reposition the sheath.

Objects, features, and advantages of the present invention will become apparent upon reading the following specification, when taken in conjunction with the drawings and the appended claims.

BRIEF DESCRIPTION OF THE DRAWINGS

The invention will now be described with reference to the following drawings, wherein.

DETAILED DESCRIPTION OF THE DISCLOSED EMBODIMENT

Figure 1:
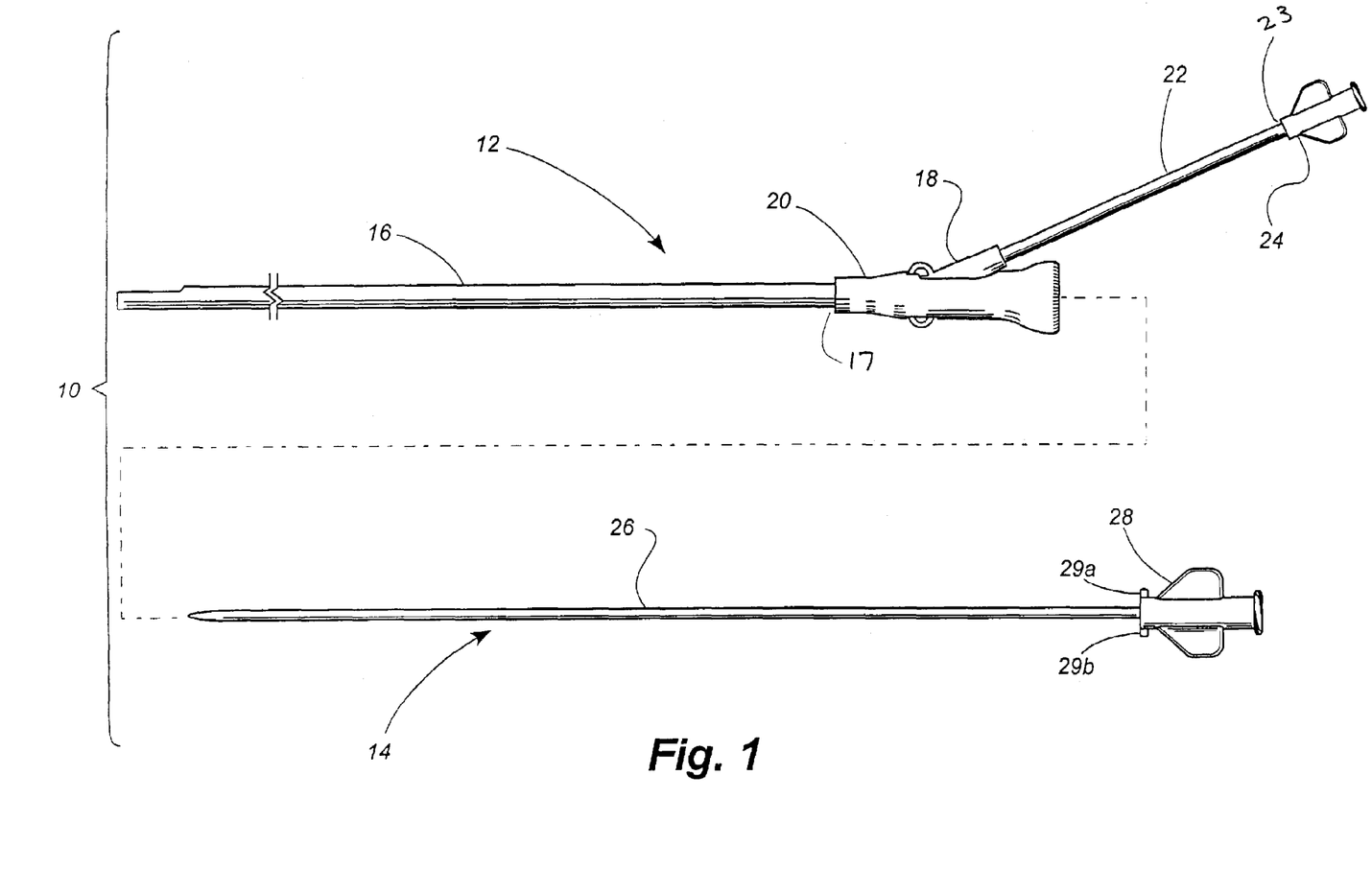
FIG. 1 is an exploded view of a ureteral access sheath according to a first disclosed embodiment.

Referring now to the drawings, in which like numerals indicate like elements throughout the several views, FIG. 1 depicts a ureteral access sheath according to a disclosed embodiment of the present invention. The ureteral access sheath 10 comprises a sheath assembly 12 and a dilator assembly 14, which fits within the sheath assembly 12 when the ureteral access sheath 10 is being positioned within a patient.

The sheath assembly 12 includes an elongated sheath tubing 16 having a distal end 17 and a proximal end coupled to a hub 18. The hub 18 is partially encased within an elastomeric cover 20. A leader tube 22 is also coupled to the hub 18. A female luer fitting 24 is mounted to the proximal end 23 of the leader tube 22.

The dilator assembly 14 comprises a dilator tubing 26 having a dilator luer 28 attached to the proximal end of the tubing. A pair of locking tabs 29a, b are formed or otherwise provided at a distal portion of the luer 28.

FIG. 1 is intended to provide only a general overview of the ureteral access sheath 10 of the present invention. Each of the components of the sheath assembly 12 will be more fully described with respect to additional drawing figures.

Figure 2:
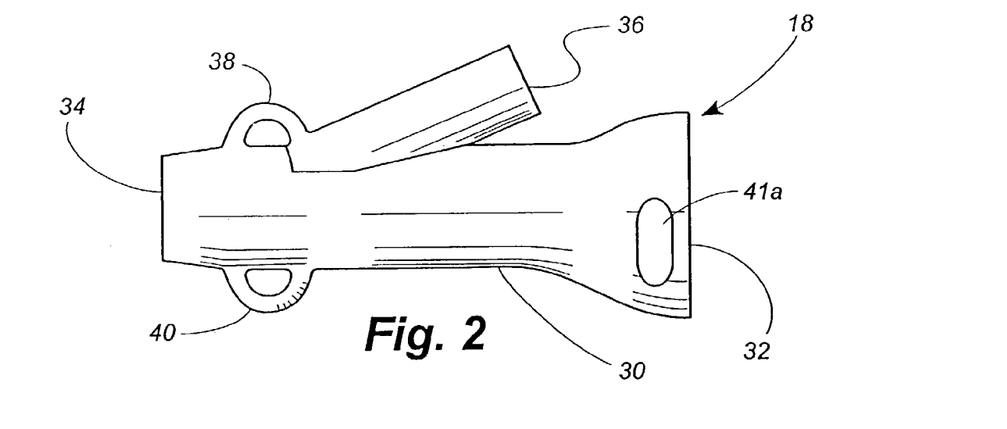
FIG. 2 is a side view of a hub of the ureteral access sheath of FIG. 1.

Referring now to FIG. 2, the hub 18 comprises a generally cylindrical main body portion 30 having a proximal end 32 and a distal end 34. A fitting 36 branches off from the main body portion 30. As will be explained in more detail below, the fitting 36 provides access to an auxiliary or secondary lumen of the sheath tubing 16. A pair of rings 38, 40 extend from the upper and lower edges of the main body portion 30 adjacent the distal end 34. The rings 38, 40 provide a means by which sutures can be attached to the hub 18 to secure the sheath assembly 12 to a surgical drape. A pair of mutually opposed locking slots 41a, b are formed or otherwise provided adjacent to the proximal end 32 of the hub 18. The function of the locking slots 41a, b is to cooperate with the locking tabs 29a, b on the luer 28 of the sheath assembly 12 to permit the luer 28 to lock to the hub 18.

Figure 3:
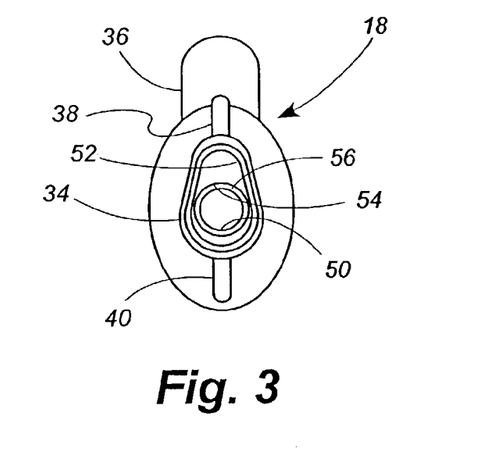
FIG. 3 is a front view of the hub of FIG. 2.
Figure 4:
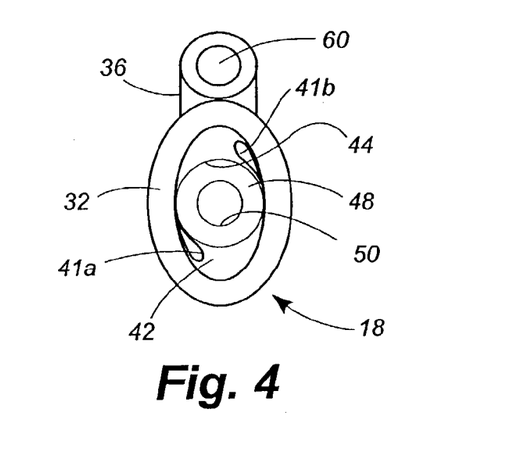
FIG. 4 is a rear view of the hub of FIG. 2.
Figure 5:
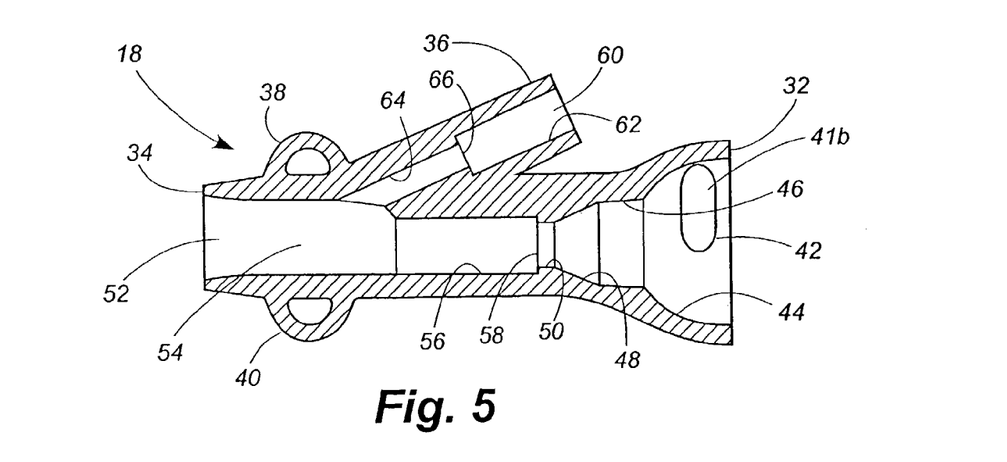
FIG. 5 is a side cutaway view of the hub of FIG. 2.
Figure 6:
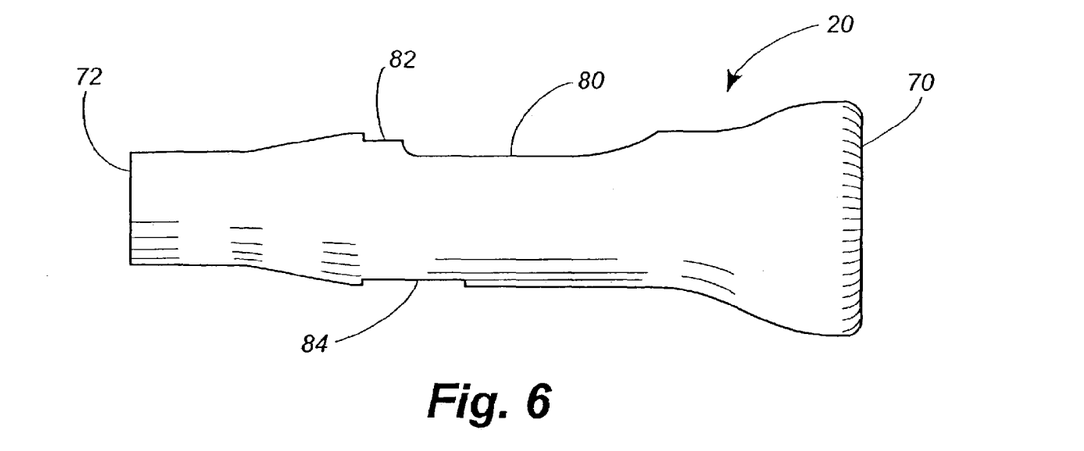
FIG. 6 is a side view of an elastomeric cover of the ureteral access sheath of FIG. 1.
Figure 7:
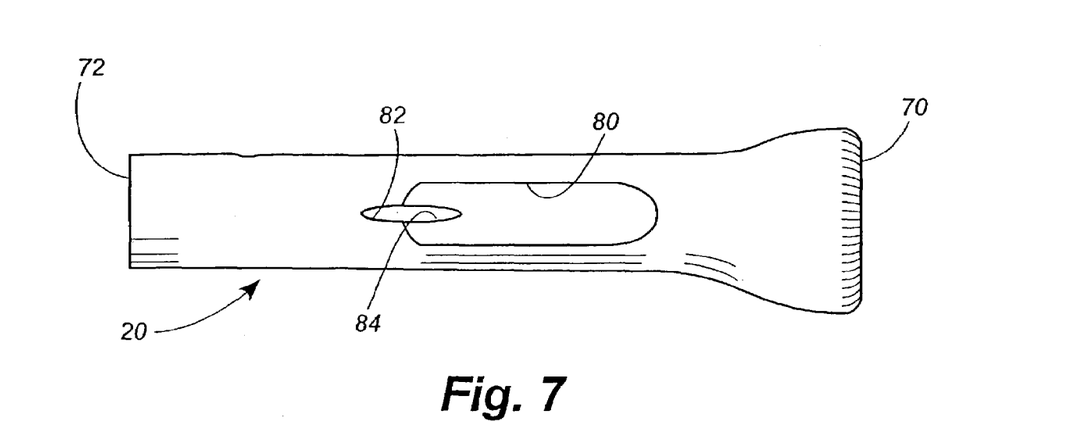
FIG. 7 is a top view of the elastomeric cover of FIG. 6.
Figure 8:
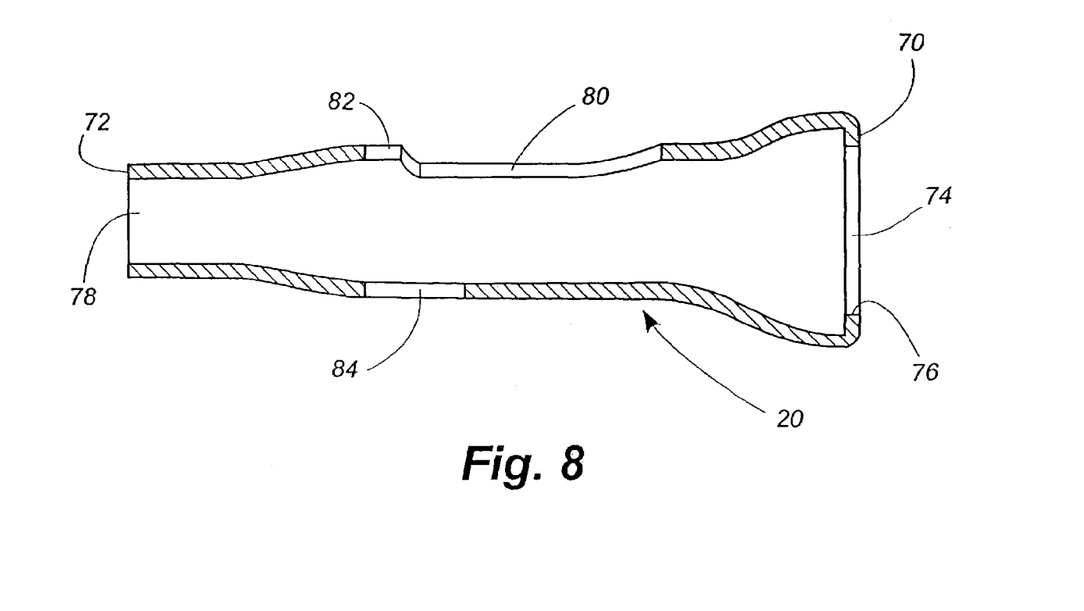
FIG. 8 is a side cutaway view of the elastomeric cover of FIG. 6.
Figure 9:
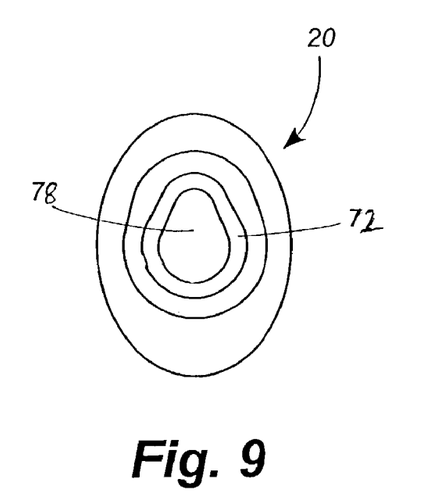
FIG. 9 is a front view of the elastomeric cover of FIG. 6.
Figure 10:
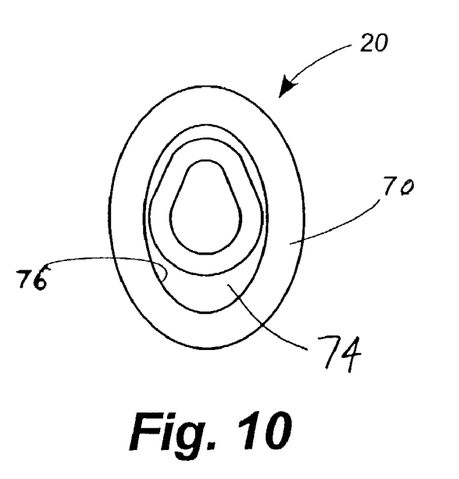
FIG. 10 is a rear view of the elastomeric cover of FIG. 6.
Figure 11:
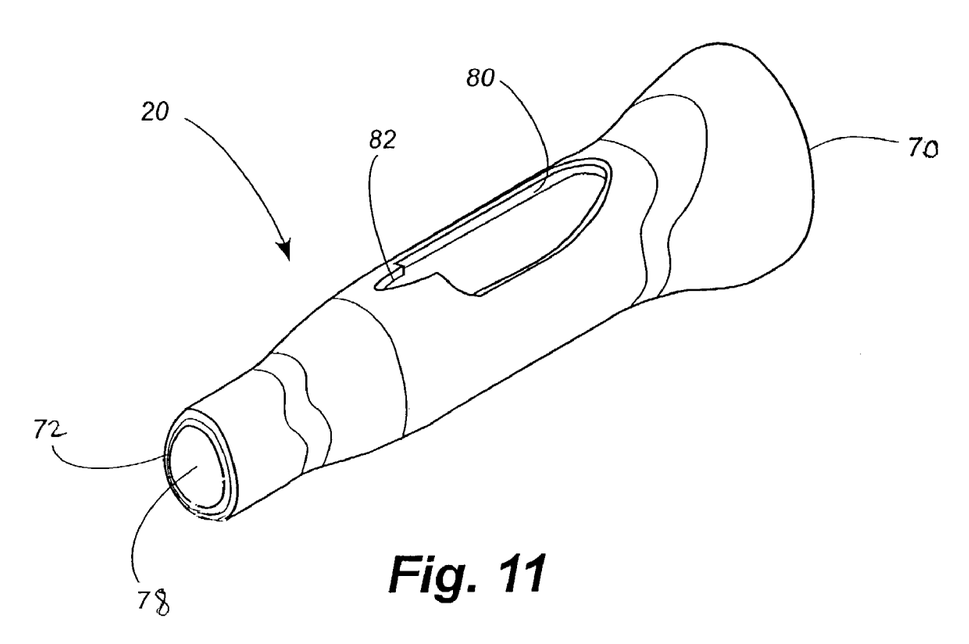
FIG. 11 is an isometric view of the elastomeric cover of FIG. 6.

The interior structure of the hub 18 is illustrated in FIGS. 3-5. An oblong opening 42 is formed in the proximal end 32 of the hub 18. Within the oblong opening 42, a bowl-shaped funnel portion 44 feeds into tapered section 46. The tapered section 46 in turn feeds into a second tapered section 48, which narrows into a short cylindrical bore 50. In the disclosed embodiment, the tapered section 46 is preferably configured to mate with the luer tip of a conventional Toomey syringe, for reasons that will be explained below.

At the distal end 34 of the hub 18, an ovate opening 52 is vertically elongated and is wider and its lower end than its upper end. An oblong front chamber 54 communicates with a cylindrical bore 56. The cylindrical bore 56 coaxially joins the smaller cylindrical portion 50. A step 58 is formed where the larger cylindrical bore 56 meets the smaller cylindrical portion 50.

Referring now to the fitting 36 at the upper end of the hub 18, an opening 60 is formed in the end of the fitting. Within the opening 60 is a cylindrical bore 62. The cylindrical bore 62 coaxially joins a smaller cylindrical bore 64, creating a step 66 where the bores 62, 64 join. The opposite end of the smaller cylindrical bore 64 opens into the chamber 54 in the distal end 34 of the hub 18.

Referring now to FIGS. 6-11, the elastomeric cover 20 has a proximal end 70 and a distal end 72. The proximal end 70 includes a vertically elongated opening 74 surrounded by an inwardly extending peripheral flange 76. The vertically elongated opening 74 corresponds in size and shape to the oblong opening 42 in the proximal end 32 of the hub 18. Similarly, a vertically elongated opening 78 in the distal end 72 of the elastomeric cover 20 generally corresponds in size and shape to the ovoid opening 52 in the distal end of the hub 18.

An elongated opening 80 is formed in the upper surface of the elastomeric cover 20. The opening 80 is rounded at its proximal and distal ends. The distal end of the opening 80 is in communication with a notch 82. A short elongated opening 84 is formed in the lower surface of the elastomeric cover 20.

Figures 12, 13:
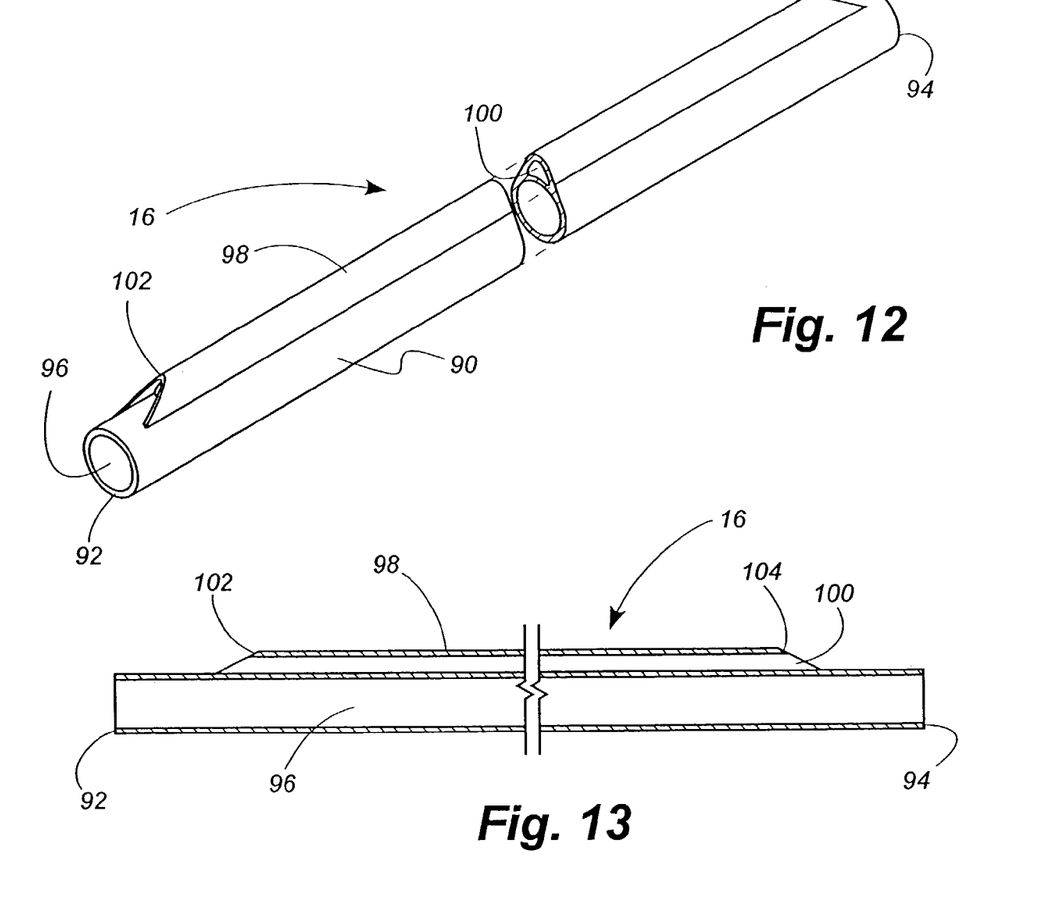
FIG. 12 is an isometric view of the sheath tubing of the ureteral access sheath of FIG. 1.
FIG. 13 is a side cutaway view of the sheath tubing of FIG. 12.
Figure 14:
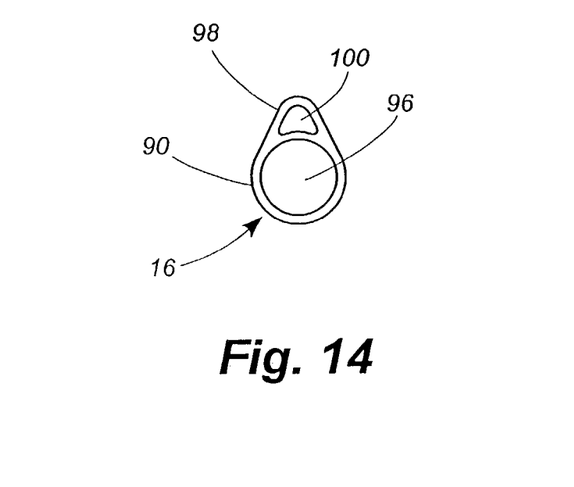
FIG. 14 is an end view of the sheath tubing of FIG. 12.

FIGS. 12-14 illustrate the sheath tubing 16 of the sheath assembly 12. The sheath tubing 16 comprises a substantially circular tube 90 having a distal end 92 and a proximal end 94. The tube 90 defines a main lumen 96. In a preferred embodiment the main lumen 96 is substantially circular in cross-section. A U-shaped housing 98 sits atop the tube 90 and defines a secondary lumen 100 disposed above the main lumen 90. The housing 98 terminates at distal and proximal locations 102, 104 respectively, that are spaced inward from the ends of the tube 90. Thus the secondary lumen 100 terminates at locations which are axially displaced inward from the ends of the main lumen 96.

As illustrated in FIGS. 12-14, the disclosed embodiment comprises a tube 90 that is substantially circular in cross-section, a main lumen 96 that is substantially circular in cross-section, and a secondary lumen 100 that is substantially crescent-shaped in cross-section. However, it will be understood that the invention is not limited to these shapes, and that tubes, main lumens, and secondary lumens of other cross-sectional configurations may be employed as may be expeditious for particular surgical applications or convenient or for manufacturing purposes.

Figure 15:
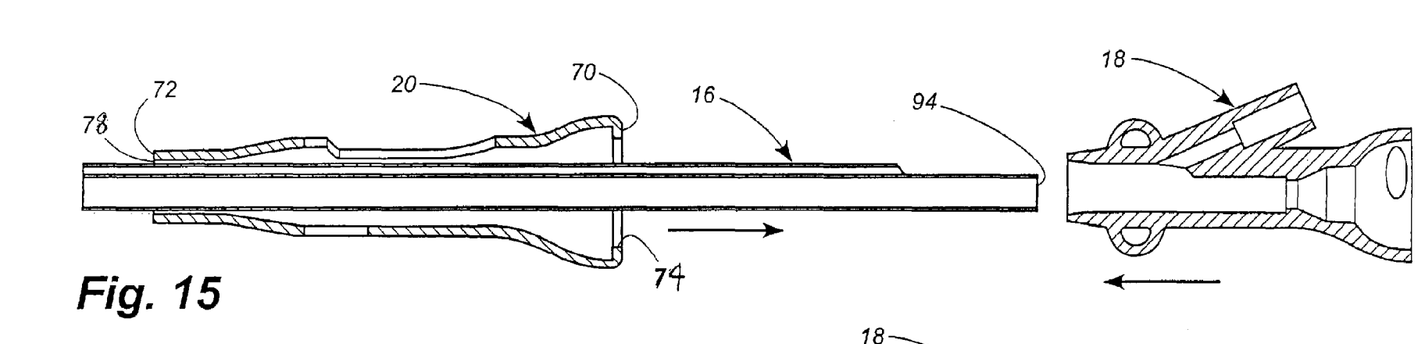
FIG. 15 is a side cutaway view illustrating the assembly of the sheath tubing of FIG. 12 through the elastomeric cover of FIG. 6 and into the hub of FIG. 2.
Figure 16:
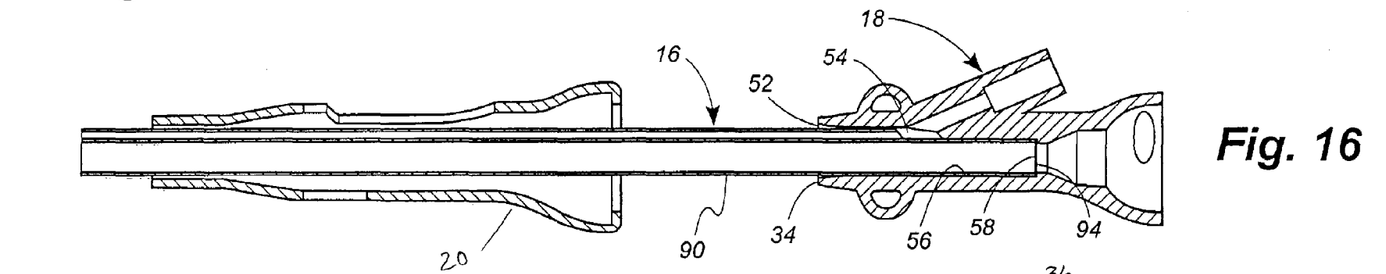
FIG. 16 is a side cutaway view of the hub of FIG. 2 mounted onto the end of the sheath tubing of FIG. 12.

Assembly of the ureteral access sheath 10 will now be explained with reference to FIGS. 15-18. Referring first to FIG. 15, the proximal end 94 of the sheath tubing 16 is inserted through the opening 78 in the distal end 72 of the elastomeric cover 20 and all the way through the cover 20 until the proximal end of the sheath tubing 16 protrudes from the opening 74 in the proximal end 70 of the cover 20. The hub 18 is aligned with the sheath tubing 16 as shown in FIG. 15. Then, as depicted in FIG. 16, the hub 18 is advanced onto the sheath tubing 16. The proximal end 94 of the sheath tubing 16 enters the opening 52 at the distal end 34 of the hub 18. As the hub 18 is advanced further, the proximal end 94 of the tube 90 passes through the front chamber 54 of the hub 18 and enters the cylindrical bore 56. When the hub 18 has been fully advanced, the proximal end 94 of the tube 90 abuts the stop 58 at the rearward end of the cylindrical bore 56, as shown in FIG. 16.

Figure 17:
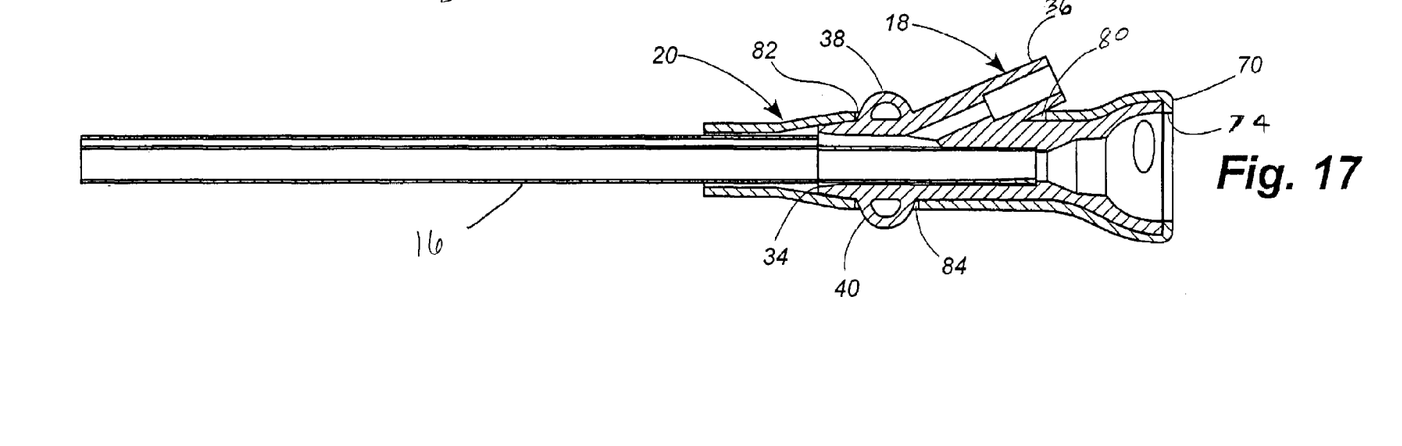
FIG. 17 is a side cutaway view of the assembly of FIG. 16 with the elastomeric cover of FIG. 6 fitted over the hub of FIG. 2.

Next, as illustrated in FIG. 17, the elastomeric cover 20 is drawn rearward over the hub 18. The distal end 34 of the hub 18 passes into the opening 74 in the proximal end 70 of the elastomeric cover 20. The elastomeric cover 20 is drawn rearward until the ring 38 on the upper surface of the hub resides within the notch 82 in the upper surface of the elastomeric cover 20, and the ring 40 on the lower surface of the hub resides within the short elongated opening 84 in the lower surface of the elastomeric cover. The fitting 36 extends through the elongated opening 80 in the upper surface of the elastomeric cover 20. When the hub 18 has been fully received into the elastomeric cover 20, the elastomeric cover snugly fits to the contours of the outer surface of the hub, as shown in FIG. 17.

Figure 18:
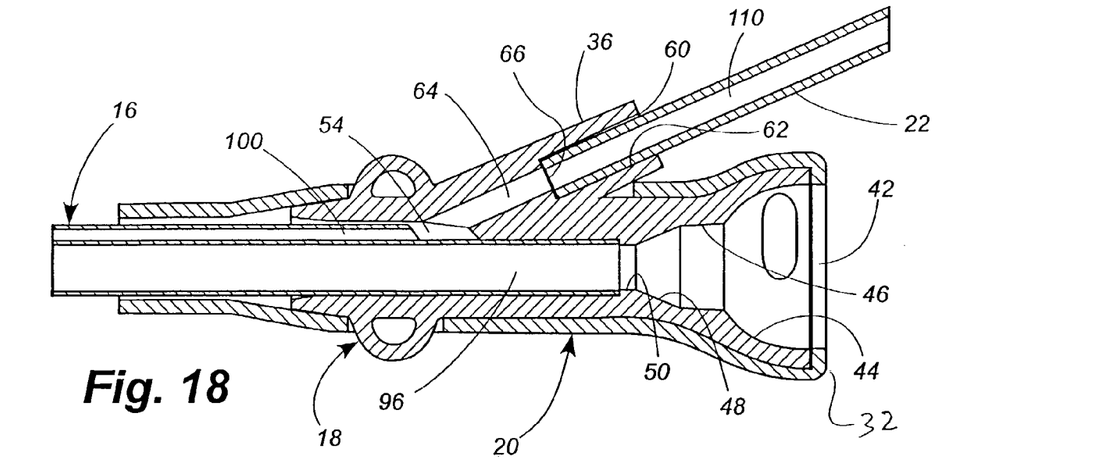
FIG. 18 is a side cutaway view of the assembly of FIG. 17 with a leader tube coupled to the hub of FIG. 2.

Referring now to FIG. 18, the leader tube 22 has been inserted into the hub 18. The end of the leader tube 22 is inserted into the opening 60 of the fitting 36 at the upper end of the hub 18. The end of the leader tube is advanced through the cylindrical bore 62 until it confronts the stop 66. The lumen 110 of the leader tube is in fluid communication with the secondary lumen 100 of the sheath tubing 16 by way of the smaller cylindrical bore 64 and the upper portion of the chamber 54 of the hub 18. The main lumen 96 of the sheath tubing 16 is in fluid communication with the opening 42 in the proximal end 32 of the hub 18 by way of the bore 50, second tapered section 48, tapered section 46, and funnel portion 44.

Figure 19:
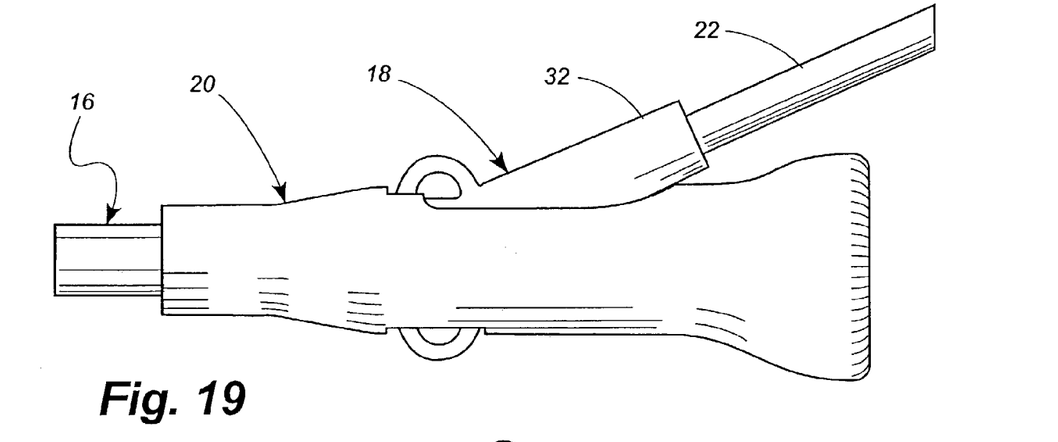
FIG. 19 is a side view of the assembly of FIG. 18.

FIG. 19 is a side view of the assembly of FIG. 18. The hub 18 is encased by the elastomeric cover 20. The leader tube 22 extends from the fitting 32 of the hub 18. The sheath tubing 16 extends from the distal end of the hub 18.

Figure 20:
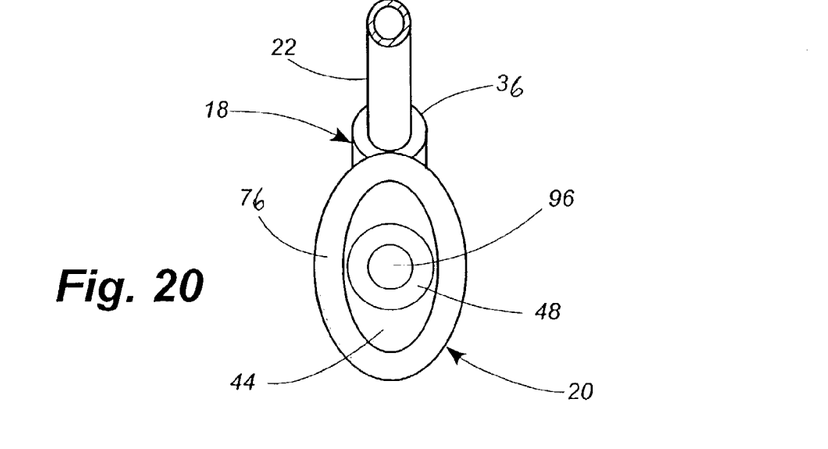
FIG. 20 is an end view of the assembly of FIG. 18.

FIG. 20 is a rear view of the assembly of FIG. 18. Once again, the hub 18 is encased by the elastomeric cover 20, and the leader tube 22 extends from the fitting 3 6 oft he hub 18. The flange 76 of the elastomeric cover 20 conceals the rear edge (element 32 in FIG. 4) of the hub 18. The funnel portion 44 and the tapered portion 48 of the hub 18 are visible. The main lumen 96 of the sheath tubing is also visible.

Figure 21:
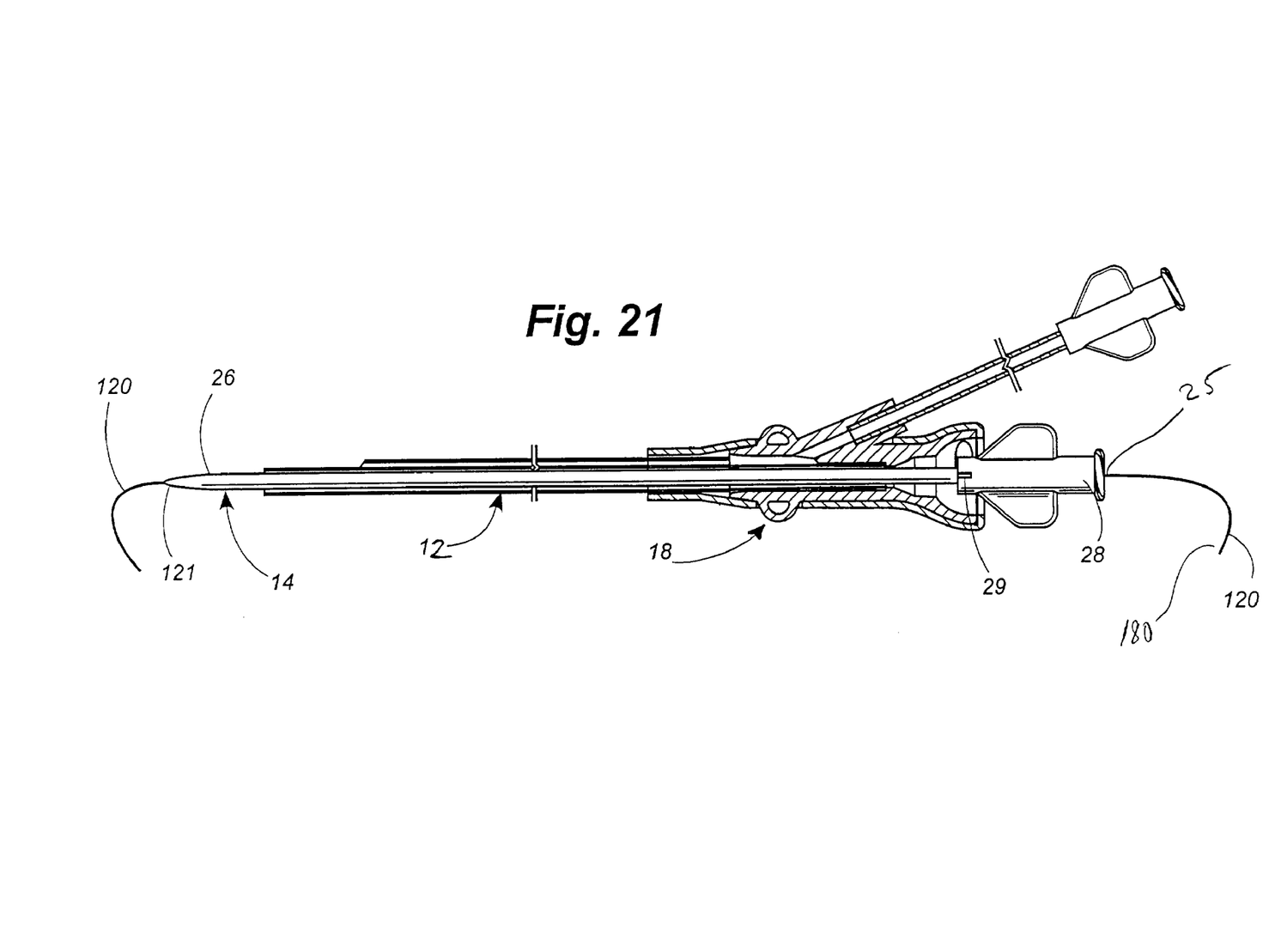
FIG. 21 is a side cutaway view of the ureteral access sheath of FIG. 1 with a guidewire extending through the main channel of the sheath.
Figure 22:
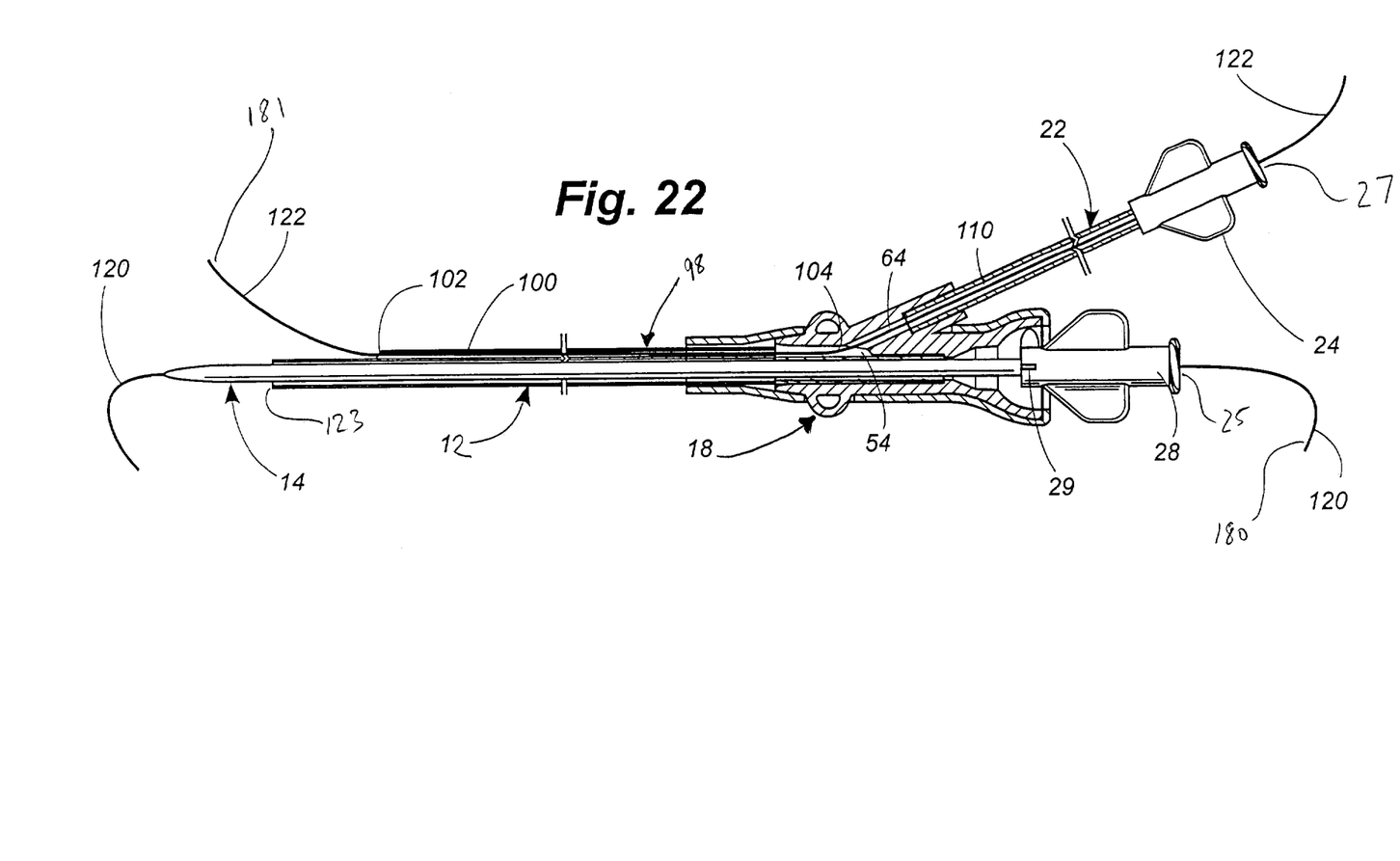
FIG. 22 is a side cutaway view of the ureteral access sheath of FIG. 21 with the first guidewire extending through the main channel of the sheath and a safety guidewire extending through the secondary channel of the sheath.
Figure 23:
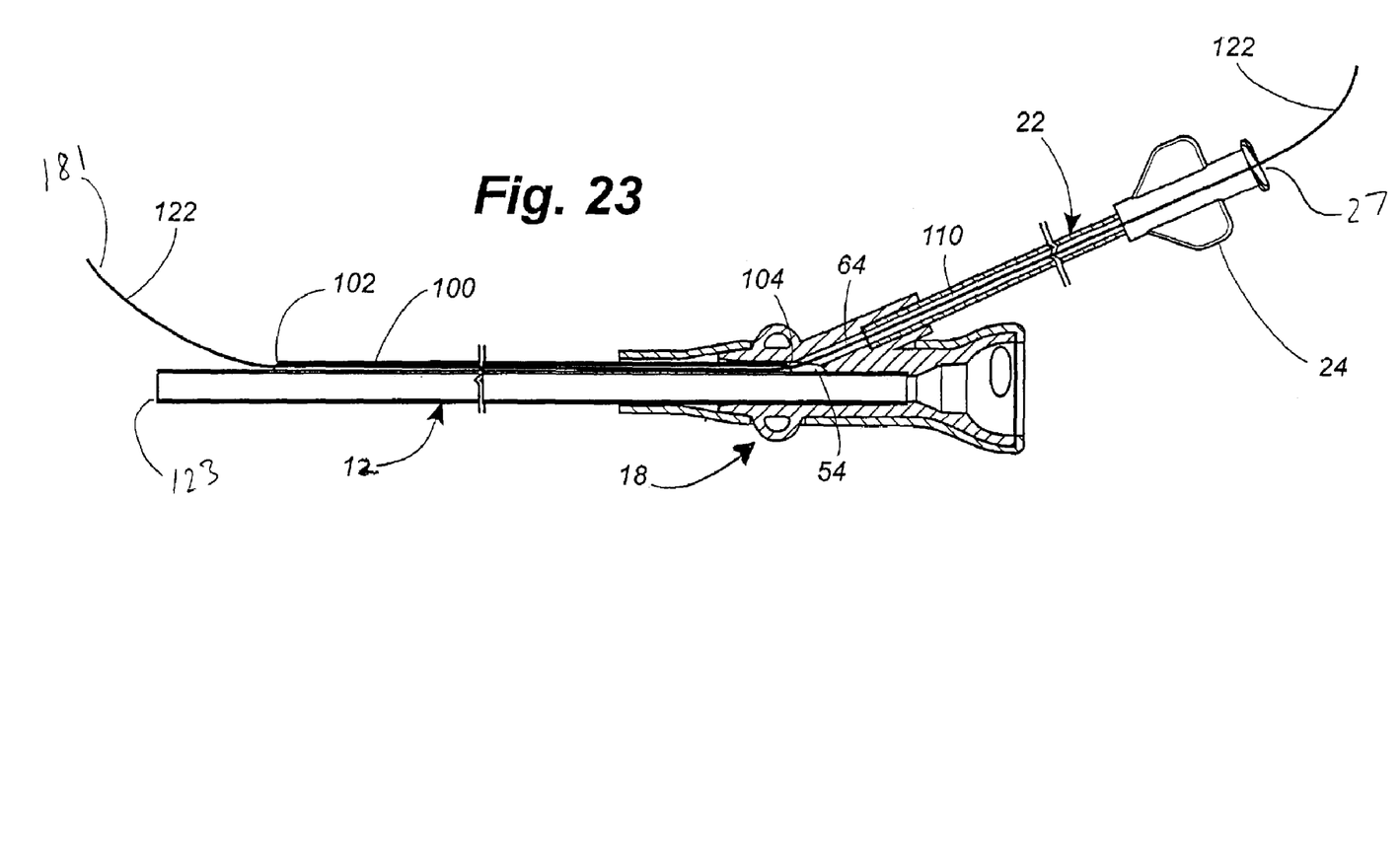
FIG. 23 is a side cutaway view of the ureteral access sheath of FIG. 22 with the first guidewire and dilator withdrawn from the main channel of the sheath and the safety guidewire remaining in place within the secondary channel of the sheath

Use of the ureteral access sheath 10 to provide a working channel will now be explained with reference to FIGS. 21-23. Steps 1-4 are conventional and hence are not shown in the drawings.

1. A cystoscope is inserted into the patient's urethra and advanced into the bladder, where the ureteral orifices are identified.
2. Using the cystoscope, a guidewire 120 is inserted into the ureteral orifice.
3. Using fluoroscopy, the guidewire 120 is advanced through the ureter and into the kidney.
4. With the guidewire 120 carefully held in place, the cystoscope is removed over the guidewire.
5. Referring now to FIG. 21, the dilator assembly 14 is placed within the main lumen of the sheath assembly 12. The dilator assembly 14 is inserted into the sheath assembly 12 with the locking tab 29a of the dilator luer 28 oriented vertically. Then, when the dilator luer 28 is seated within the hub 18 of the sheath assembly 12, the dilator luer 28 is rotated 90° clockwise, and the locking tabs 29a, b on the dilator luer engage the locking slots 41a, b at the proximal end 32 of the hub 18 to lock the dilator assembly 14 to the sheath assembly 12.
6. With further reference to FIG. 21, the proximal end 180 of the guidewire 120 is inserted into the distal end 121 of the dilator tubing 26. The guidewire 120 is advanced through the dilator tubing 26 and exits through the proximal end 25 of the dilator luer 28.

7. The sheath assembly 12 with dilator assembly 14 in place is advanced over the guidewire 120 and into the ureter. Advancement and position of the ureteral access. sheath is usually verified with fluoroscopy.

8. Referring now to FIG. 22, with the sheath assembly 12 in position with its distal end 123 within the ureter, the distal end 181 of a safety guidewire 122 is fed into the opening in the proximal end 27 of the luer fitting 24. The safety guidewire 122 is advanced through the lumen 110 of the leader tube 22 and into the small cylindrical bore 64, from where it enters the chamber 54 of the hub 18. The distal end 27 of the safety wire 122 then enters the secondary lumen 100 at the proximal end 104 of the housing 98 and traverses the length of the secondary lumen, exiting at the distal end 102 of the housing 98.

9. With the safety guidewire 122 thus positioned, the dilator assembly 14 and main guidewire 120 are removed from the sheath assembly 12, as shown in FIG. 23.

Figure 24:
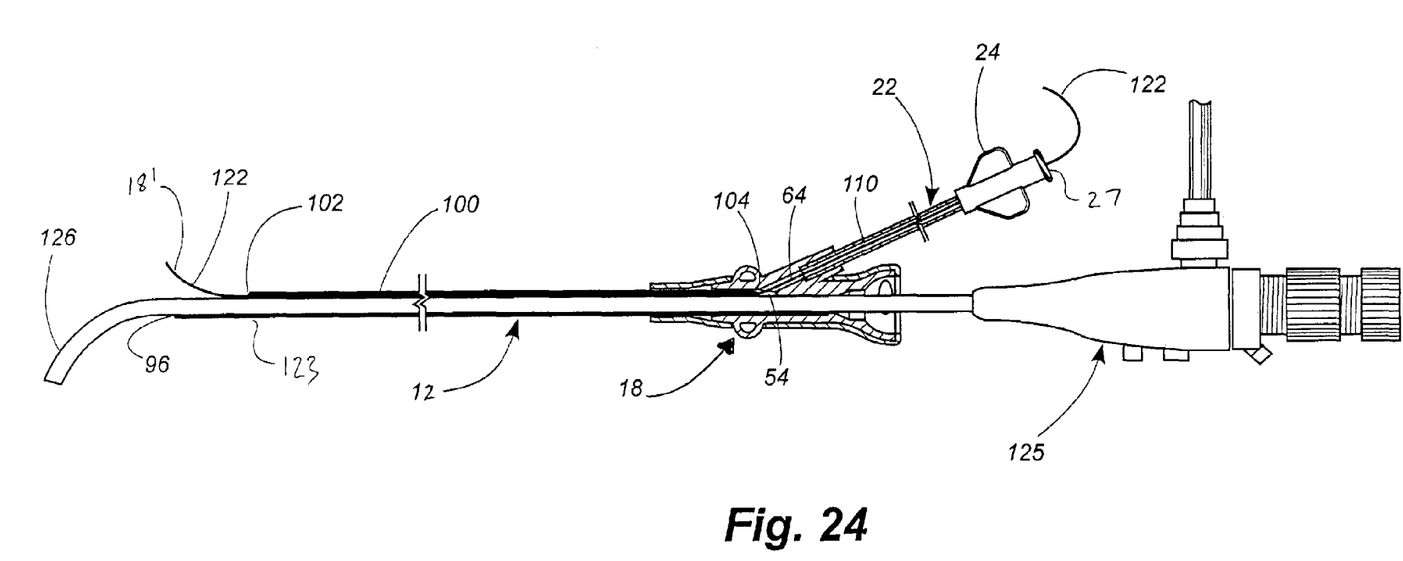
FIG. 24 is a side cutaway view of the ureteral access sheath of FIG. 23 with an endoscope sheath positioned within the main lumen of the ureteral access sheath.

Once the sheath assembly is in place to provide a working channel, a surgical procedure can commence. For example, a ureteroscope 125 has its distal end 126 introduced into the proximal end of the main lumen 96 of the sheath assembly 12, as shown in FIG. 24. The ureteroscope 125 is advanced through the sheath assembly 12 to the target site until the distal end 126 of the ureteroscope resides adjacent the target site. A surgical instrument, such as a grasper for crushing and removing calculi, is inserted through the working channel of the ureteroscope 125 and used in the conventional manner. When it becomes necessary to irrigate the surgical field, an irrigation means is coupled to the female luer fitting 24 at the end of the leader tube 22, and an irrigation fluid is infused through the secondary lumen 100. The irrigation means can comprise, for example, a syringe, a bag of saline solution hung from an IV pole, an irrigation system including rollers for pressurized expulsion of saline solution from a bag, or the like. To facilitate coupling an irrigation means to the secondary lumen 100 while the safety guidewire 122 is still in place, a Y-fitting can be coupled to the female luer 24, the safety guidewire fed through one of the branches of the Y-fitting, and the irrigation means coupled to the other branch of the Y-fitting. Because the safety guidewire 122 occupies only a small portion of the cross section of the secondary lumen 100, irrigation can be effected through the same secondary lumen occupied by the guidewire.

Figure 25:
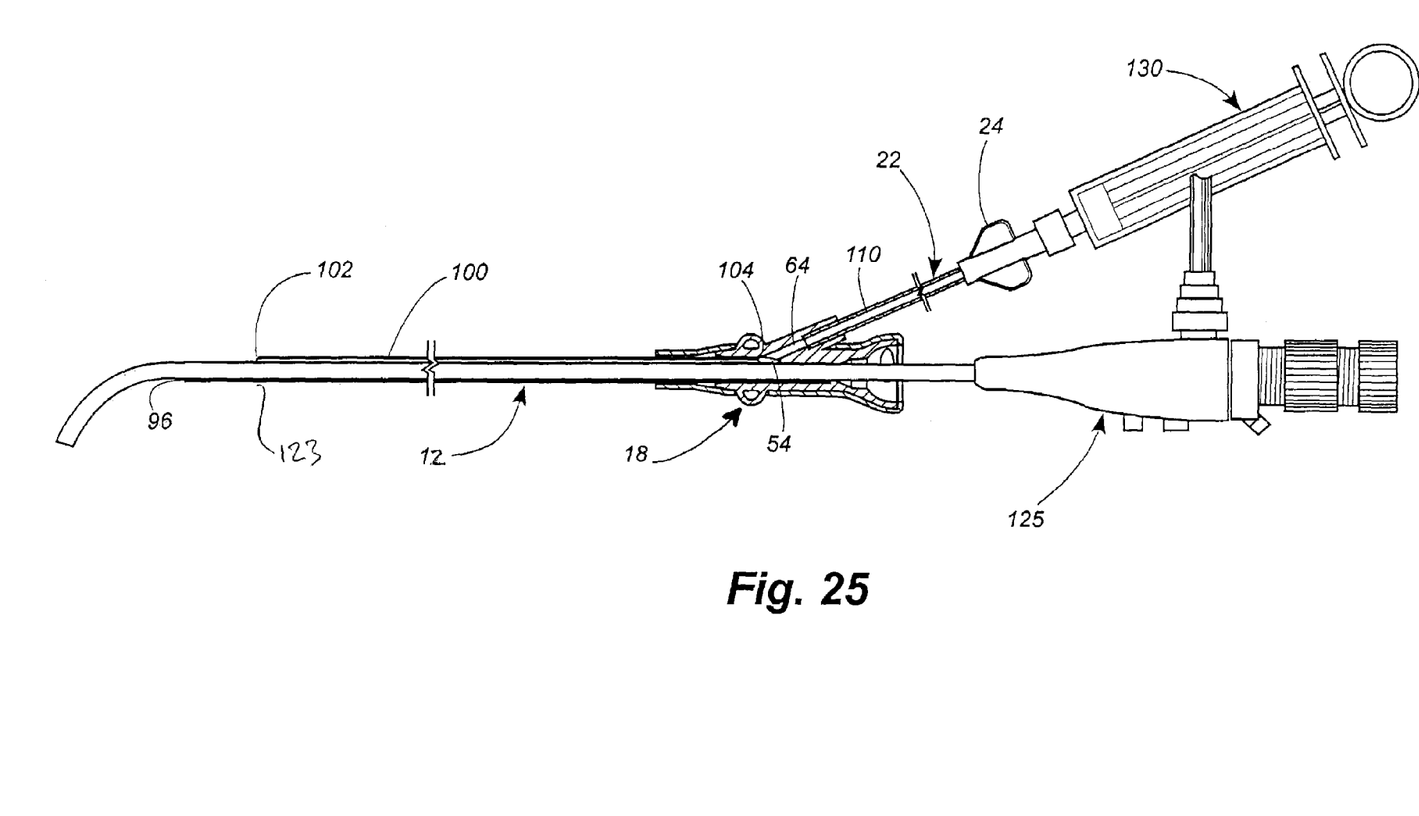
FIG. 25 is a side cutaway view of the ureteral access sheath of FIG. 1 with the dilator removed and with an endoscope sheath positioned within the main lumen of the ureteral access sheath and an irrigation syringe coupled to the secondary lumen of the sheath.

FIG. 25 shows an alternate configuration wherein the sheath assembly 12 is used to accommodate an endoscope 125 in the main working channel 96 and an irrigation means such as a syringe 130 is coupled to the secondary lumen 100. Even with the working channel of the ureteroscope 125 almost completely occupied by a surgical instrument, and even with the main working channel 96 of the sheath assembly 12 almost completely occupied by the ureteroscope 125, the surgical field can still be irrigated efficiently by infusing the irrigation fluid through the secondary lumen 100.

Figure 26:
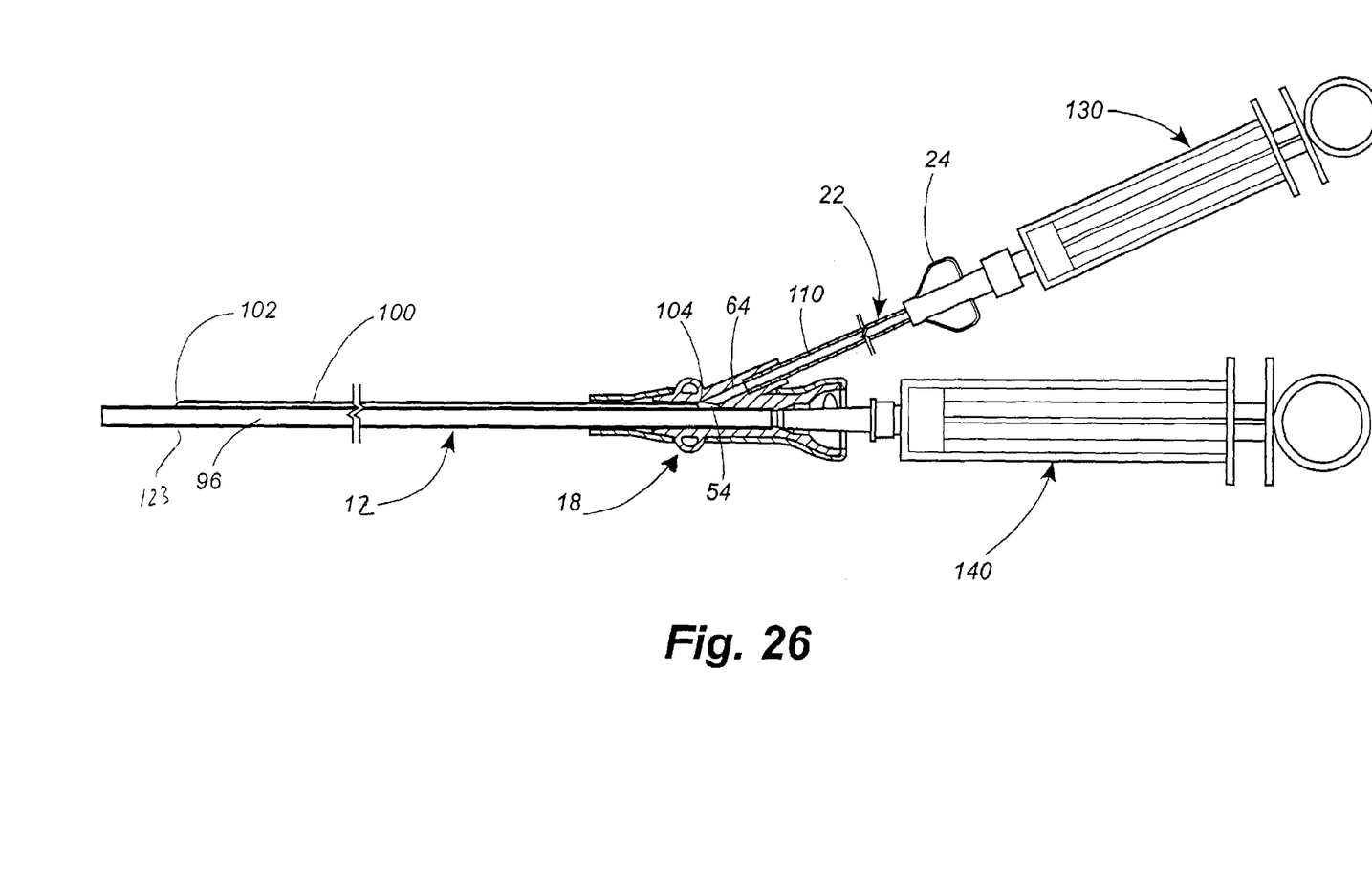
FIG. 26 is a side cutaway view of the ureteral access sheath of FIG. 1 with the dilator removed and with an aspiration syringe coupled to the main lumen of the ureteral access sheath and an irrigation syringe coupled to the secondary lumen of the sheath.

FIG. 26 shows yet another alternate configuration wherein the sheath assembly 12 is used to accommodate an aspiration means such as a Toomey syringe 140 coupled to the main working channel 96, and an irrigation means such as a syringe 130 coupled to the secondary lumen 100. With this configuration, simultaneous irrigation and aspiration can be accomplished, which can create a turbulent effect in the operative field that is useful for removing particles and debris.

The ureteral access sheath 12 of the disclosed embodiment thus provides a number of advantages over known prior art ureteral access sheaths. Because of the dual lumens 96, 100, the sheath assembly 12 can be configured as follows:

Device-Device. Both lumens can be occupied by medical devices. While the main working channel will most often be occupied by a ureteroscope, the secondary channel can be occupied by a safety guidewire, a laser fiber, a stone basket, a grasper, or any other medical device suitable to the procedure being performed. In the case of placing a safety guidewire in the secondary lumen, the sheath assembly 12 can be rapidly repositioned without the need for multiple backloads.

Device-Irrigation. The main working channel can be occupied by a ureteroscope, and the secondary working channel can be coupled to a source of irrigation such as a syringe, irrigation bag, irrigation system, or the like. Thus even when the main working channel of the ureteroscope is almost completely occupied by a surgical instrument, the surgical field can be irrigated efficiently by infusing the irrigation fluid through the secondary lumen.

Device-Device/Irrigation. The main working channel can be occupied by an instrument such as a ureteroscope 125. A Y-fitting can be attached to the female luer 24 of the leader tube 22. The safety guidewire 122 can be fed through the opening in one branch of the Y-fitting, and an irrigation means can be coupled to the other branch of the Y-fitting so that irrigation can be achieved while the safety guidewire is still in place within the secondary lumen 100.

Irrigation-Irrigation. The main working channel can be coupled to an aspiration means such as a Toomey syringe by locking the luer of the syringe into the tapered section 46 of the hub 18, and the secondary channel can be coupled to a source of irrigation such as a syringe, irrigation bag, irrigation system, or the like. Thus it is possible to irrigate the operative field through the secondary channel while aspirating the field through the main channel, setting up a turbulent flow in the operative field which is helpful in removing particles and debris.

Figures 27, 28, 29:
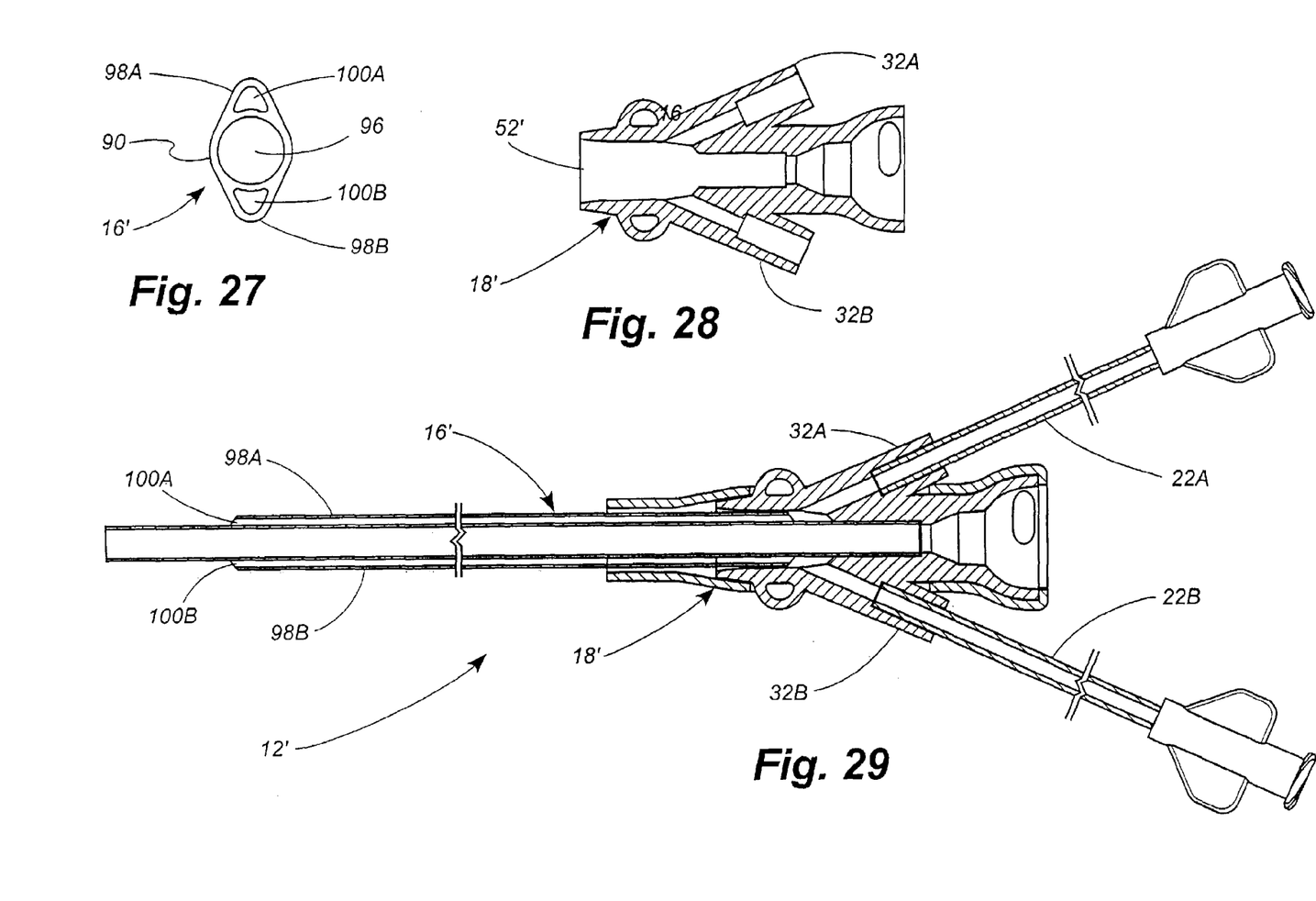
FIG. 27 is an end view of a sheath tubing for use with the hub of FIG. 28.
FIG. 28 is a side cutaway view of a hub of an alternate embodiment of a ureteral access sheath.
FIG. 29 is a side cutaway view of an alternate embodiment of eight ureteral access sheath comprising the hub of FIG. 28 and the sheath tubing of FIG. 27.

FIG. 27 illustrates an alternate embodiment of a sheath tubing 16'. The sheath tubing 16' includes a first U-shaped housing 98A on top of the tube 90 and a second U-shaped housing 98B on the side of the tube opposite the first housing 98A. Two secondary lumens 100A, 100B are thus formed on opposite sides of the main lumen 96.

FIG. 28 illustrates an alternate embodiment of a hub 18' for use with the sheath tubing 16' of FIG. 27. The hub 18' differs from the hub 18 previously described in that it has two fittings 32A, 32B. In addition, the opening 52' at the forward end of the hub 18' is reconfigured to accommodate the sheath tubing 16' with two U-shaped housings 98A., 98B.

FIG. 29 depicts an alternate embodiment of a sheath assembly 12' that comprises a sheath tubing 16', a hub 18', and two leader tubes 22A, 22B. Each of the two leader tubes 22A, 22B. is in fluid communication with a separate one of the two secondary lumens 100A., 100B. In the case of the sheath tubing 16' having two secondary lumens 100A., 100B, the irrigation fluid is introduced through a secondary lumen different from the secondary lumen occupied by the guidewire. Or, a guidewire can occupy one channel while a grasper, laser fiber, or stone basket is used in the other secondary channel. As yet another option, a surgical instrument such as a grasper, stone basket, laser fiber, or the like can be used in one secondary channel while the other secondary channel is being used for irrigation. As still another option, one secondary channel can be hooked up to an irrigation means while the other secondary channel is hooked up to an aspiration means. In this manner simultaneous irrigation and aspiration to create a turbulent wash in the surgical field can be performed without removing a surgical instrument such as a ureteroscope from the main working channel.

Finally, it will be understood that the preferred embodiment has been disclosed by way of example, and that other modifications may occur to those skilled in the art without departing from the scope and spirit of the appended claims.

What is claimed is:

1. An access sheath, comprising:
a sheath assembly having a multi-lumen hub, including a fitting that provides access to a main and a secondary lumen, from which the elongated sheath extends, the sheath assembly further comprising an elongated sheath tubing that is configured for insertion into a body passage, the elongated sheath tubing including the main lumen that is configured to receive a endoscope and the secondary lumen that extends along at least a portion of the main lumen; and
a dilator assembly having a dilator tubing that is configured to be inserted into the main lumen of the elongated sheath tubing, the dilator tubing comprising an internal passage that is configured to receive a guidewire;
wherein the sheath assembly is configured to be positioned within the body passage by advancing the sheath assembly and dilator assembly over a guidewire positioned within the body passage, and then removing the guidewire and dilator assembly from the sheath assembly.

2. The access sheath of claim 1, wherein the secondary lumen extends along nearly the entire length of the main lumen.

3. The access sheath of claim 1, wherein the secondary lumen terminates at a point that is proximal of a distal end of the elongated sheath tubing.

4. The access sheath of claim 1, wherein the secondary lumen is smaller than the main lumen.

5. The access sheath of claim 1, wherein the secondary lumen is configured to receive a surgical device.

6. The access sheath of claim 5, wherein the secondary lumen is configured to receive at least one of a safety wire, a laser fiber, a stone basket, and a grasper.

7. The access sheath of claim 1, wherein the secondary lumen is configured to deliver irrigation fluid to target site.

8. The access sheath of claim 1, wherein the main lumen is defined by an elongated tube and the secondary lumen is defined by a V-shaped housing provided on the elongated tube.

9. The access sheath of claim 8, wherein the main lumen is substantially circular in cross-section and the secondary lumen is substantially crescent-shaped in cross section.

10. The access sheath of claim 9, wherein the dilator assembly includes a luer that provides access to the internal passage of the dilator tubing.

11. The access sheath of claim 10, wherein the luer includes locking tabs that are received by locking slots of the hub to lock the dilator assembly to the sheath assembly.

12. The access sheath of claim 1, wherein the sheath assembly further includes an additional secondary lumen that extends along at least a portion of the main lumen.

13. The access sheath of claim 12, wherein the additional secondary lumen terminates at a point that is proximal of a distal end of the elongated sheath tubing.

14. A method for using an access sheath within a patient body passage, the access sheath including a multi-lumen hub having a fitting that provides access to a main lumen and a secondary lumen of a sheath assembly, the method comprising:
inserting a guidewire into the patient body passage;
advancing the access sheath including the sheath assembly and a dilator assembly that is inserted in the main lumen of the sheath assembly over the guidewire;
inserting a safety wire through the secondary lumen of the sheath assembly prior to removing the guidewire and dilator assembly; and
removing the guidewire and the dilator assembly once the sheath assembly has been positioned in a desired location along the patient body passage.

15. The method of claim 14, further comprising removing the sheath assembly from the body passage without removing the safety wire, inserting the dilator assembly into the sheath assembly, advancing the sheath assembly and dilator assembly over the safety wire, inserting a second safety wire through the secondary lumen of the sheath assembly, and removing the first safety wire and the dilator assembly such that the sheath assembly is replaced within the body passage with a safety wire extending through the secondary lumen.

16. The method of claim 14, further comprising inserting a ureteroscope through the main lumen of the sheath assembly.

17. The method of claim 14, further comprising delivering irrigation fluid to a target site through the secondary lumen of the sheath assembly.

18. The method of claim 14, further comprising inserting a safety wire through the secondary lumen of the sheath assembly and delivering irrigation fluid to a target site through the secondary lumen.

* * * * *